United States Patent [19]
Pinter

[11] Patent Number: 6,132,452
[45] Date of Patent: Oct. 17, 2000

[54] METHOD AND DEVICE FOR PROMOTING ENERGY FLOW IN AN ORGANISM

[75] Inventor: Joze Pinter, Pennington, N.J.

[73] Assignee: Biomega, Inc., Pennington, N.J.

[21] Appl. No.: 09/258,296

[22] Filed: Feb. 26, 1999

Related U.S. Application Data

[63] Continuation-in-part of application No. 09/173,670, Oct. 16, 1998, which is a continuation-in-part of application No. 09/086,957, May 29, 1998, abandoned.

[51] Int. Cl.$^7$ .................................................. A61N 1/16
[52] U.S. Cl. ............................................................. 607/1
[58] Field of Search ........................... 607/7, 3, 76, 115, 607/148, 152; 606/204

[56] References Cited

U.S. PATENT DOCUMENTS

| | | |
|---|---|---|
| 4,033,054 | 7/1977 | Fukuoka . |
| 4,632,095 | 12/1986 | Libin . |
| 4,694,831 | 9/1987 | Seltzer . |
| 4,808,469 | 2/1989 | Hiles . |
| 4,841,647 | 6/1989 | Turucz . |
| 5,070,862 | 12/1991 | Berlant . |
| 5,199,876 | 4/1993 | Waldman . |

OTHER PUBLICATIONS

Maggie La Tourelle and Anthea Courtenay, Thorsons Introductory Guide to Kinesiology, Harper Collins Publisher, pp. 14–23, 51–52, (1992).

Mildred Carter and Tammy Weber, "Healing Yourself with Foot Reflexology", Prentice–Hall Inc., pp. 3–6, (1977).

Mildred Carter and Tammy Weber, "Body Reflexology", Parker Publishing Co., pp. 3–5, (Rev. 1994).

Kevin and Barbara Kunz, "Hand and Foot Reflexology A Self–Help Guide", Prentice–Hall Inc., pp. 2–5, 11–12, (1987).

Richard Gherber, "Vibrational Medicine—New Choices for Healing Ourselves", Bear & Company, pp. 203–215, (1966).

*Primary Examiner*—William E. Kamm
*Attorney, Agent, or Firm*—Andrew F. Reish

[57] ABSTRACT

A device for promoting energy flow in an organism includes a metallic cross, at least one bioenergy channelizer unit having a plurality of conductive elements arranged on a dielectric material, and/or one or more mineral crystals, all mounted on a structure which is covered by a tinted covering, the device being placed adjacent to, or in proximity to, the organism. The conductive elements are disposed on the dielectric material in a predetermined spatial relationship. The device flanks across predetermined regions or structures of the organism, for example, hands, arms, feet, legs, torso, back, or the entire body, so as to overlay singular or multiple energy pathways called meridians, each relating to specific organs, glands or systems of the organism. The first conductive element and/or the metallic cross transmits the energy along from the first reflex point toward a second conductive element of the conductive elements. The second conductive element and/or metallic cross transmits the energy to a second reflex point in the vicinity of at least one of the first meridian and a second meridian in the organism, whereby healthy flow of energy throughout the organism energy is substantially increased. The method utilizes the device to promote and enhance healthy flow of energy throughout the organism.

30 Claims, 4 Drawing Sheets

METHOD AND DEVICE FOR PROMOTING ENERGY FLOW IN AN ORGANISM

This application is a continuation-in-part of application Ser. No. 09/173,670 filed on Oct. 16, 1998, which is a continuation-in-part of application Ser. No. 09/086,957 filed on May 29, 1998 and now abandoned, the entire contents of each being hereby incorporated by reference.

BACKGROUND OF THE INVENTION

1. Field of the Invention

The present invention relates to a method and device for promoting healthy flow of energy throughout an organism. The method and device employ a metallic cross, one or more units of conductive elements arranged on a dielectric material, and/or one or more mineral crystals, all mounted onto a structure which is covered by a tinted covering, the combination being flanked adjacent to or placed against the organism. Portions of the device are associated with reflex points along one or multiple energy pathways called meridians, each relating to specific organs, glands or systems of the organism.

2. Description of the Background Art

Various forms of natural medicine exist today. Two forms of natural medicine which have received much attention from the conventional modern scientific medical community as well as the natural medicine communities are kinesiology and reflexology. Both of these forms of natural medicine focus on energy flow throughout an organism. This energy flow is often referred to as "subtle energy" which is drawn to systems of energy within and around the body.

Subtle energy is similar or analogous to Qi (pronounced chi) of Chinese acupuncture and other natural healing techniques which focus on a universal life-force that is vital to the health of the mind and body of an organism. Many texts have been published on, or discuss, the subjects of reflexology and kinesiology. Such texts include at least the following: Maggie La Tourelle and Anthea Courtenay, *Thorsons Introductory Guide to Kinesiology*, Harper Collins Publisher (1992); Mildred Carter and Tammy Weber, *Healing Yourself with Foot Reflexology*, Prentice-Hall Inc. (1997); Mildred Carter and Tammy Weber, *Body Reflexology*, Parker Publishing Co. (Rev. 1994); Kevin and Barbara Kunz, *Hand and Foot Reflexology A Self-Help Guide*, Prentice-Hall Inc. (1987); and Richard Gherber, *Vibrational Medicine—New Choices for Healing Ourselves*, Bear & Company (1996).

The La Tourelle publication states that the terms "energy medicine" and "vibrational medicine" are being increasingly applied by doctors as well as natural therapists to a whole group of natural healing systems, which include acupuncture and kinesiology. The La Tourelle publication further states that subtle energy has always been seen and felt by healers and acupuncturists who are trained to read the flow of Qi through twelve specific pulses on the limb of a human body (a wrist). The pulse locations are connected with a series of energy pathways called meridians, each meridian relating to a specific organ, gland, or system of the organism. See La Tourelle publication, pages 14–15.

The La Tourelle publication explains that in kinesiology a further connection has been made between meridians and specific muscles, with which the muscles are "energetically" connected. Kinesiology uses manual muscle testing to assess the organism's energy and then applies a range of techniques to promote the healthy flow of energy throughout the organism. The La Tourelle publication explains that the ancient philosophy of Chinese medicine states that health comes from being in balance and in harmony with all things, where balance is a perfect state in which no aspect is either deficient or in excess. See La Tourelle publication, page 15.

The La Tourelle publication explains that energy circuits exist in organisms such as the human body and that energy fields extend to within two inches/five centimeters around the body. The La Tourelle publication further explains the electromagnetic problems within an organism such as a human body are caused by electrical disturbances in these energy circuits which create poor or faulty communication with the body, often giving rise to feelings or disorientation and confusion, poor coordination, dyslexia, etc. The La Tourelle publication further provides that electromagnetic factors include at least the following: ionization which involves the balance of positive and negative ions that can be breathed in by an organism which create positive and negative currents within the organism; acupuncture meridians (energy pathways) which involve fourteen meridians for over- and under-energy, each relating to a specific part or parts of the body; and right/left brain hemisphere integration.

The Carter publication drawn to foot reflexology explains that reflexology is a scientific technique of applying pressure to reflex areas or zones that have a definite affect on the normal functioning of all parts of an organism such as the human body. The same publication provides that when properly performed, a reflex massage sends stimuli to various organs, glands, and nerves in the body. The Carter publication states that tenderness at particular points, which are most commonly found in the limbs of an organism such as in the feet and the hands of the human body, may indicate congestion of energy within the organism or body. The Carter publication states that the purpose of reflexology is to promote balance and normalization, to reduce tension, to revitalize, reactivate, regenerate, heal, and bring the whole system of an organism into harmony in a state of good health, naturally.

The Gherber publication explains the presence of multi-dimensional energy fields in a living organism. These fields include subtle energy fields and electromagnetic energy fields. This publication further explains the need to balance these fields to promote good health.

Figures 3, 5:
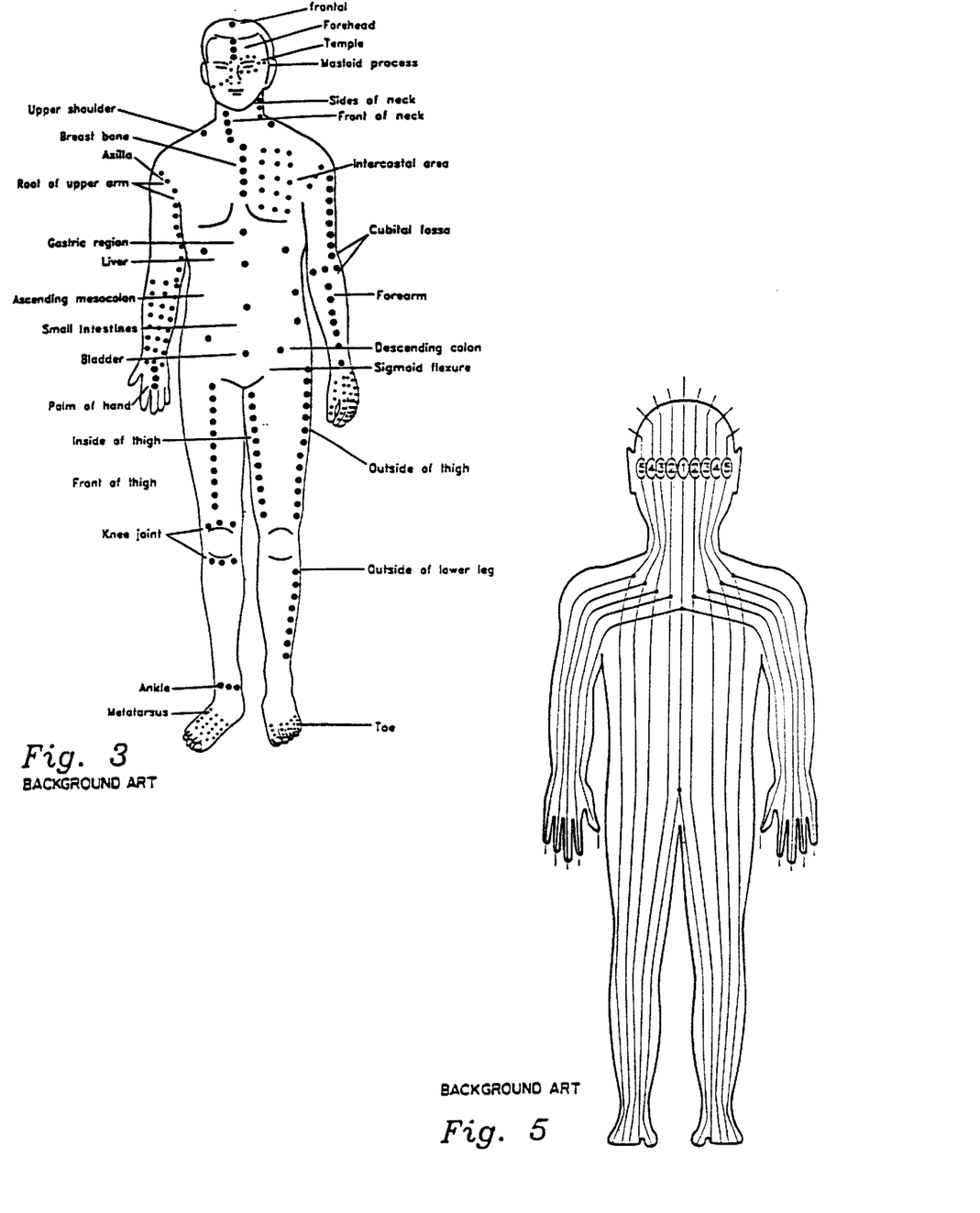
FIG. 3 provides background art of various reflex points on an organism such as the human body.
FIG. 5 shows background art on meridians or energy channels which are present in an organism such as the human body.
Figure 4:
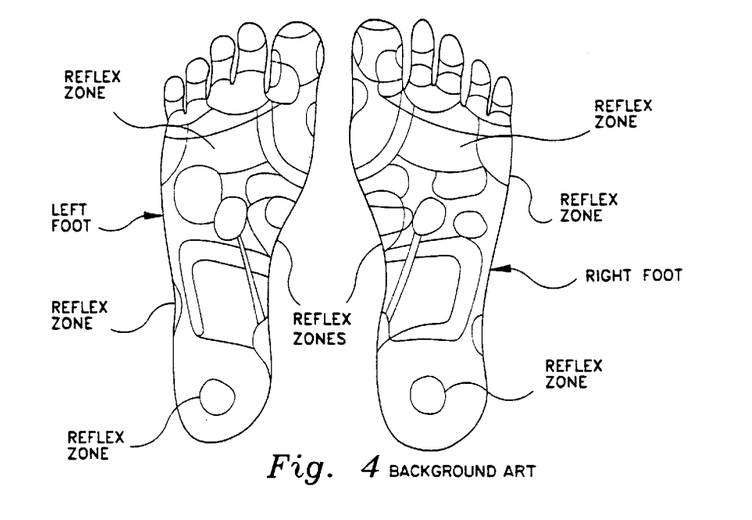
FIG. 4 shows background art of the locations of reflex points on the feet of an organism such as the human body.

U.S. Pat. No. 4,632,095 to Libin explains how various organs, nerves, and glands in a living organism such as the human body are connected with certain "reflex areas" on the bottoms of feet, hands, and other areas of the human body. FIG. 3 of the present specification, which is derived from the Libin patent, provides a typical chart showing some of the pressure points in an organism such as the human body.

Figure 6A:
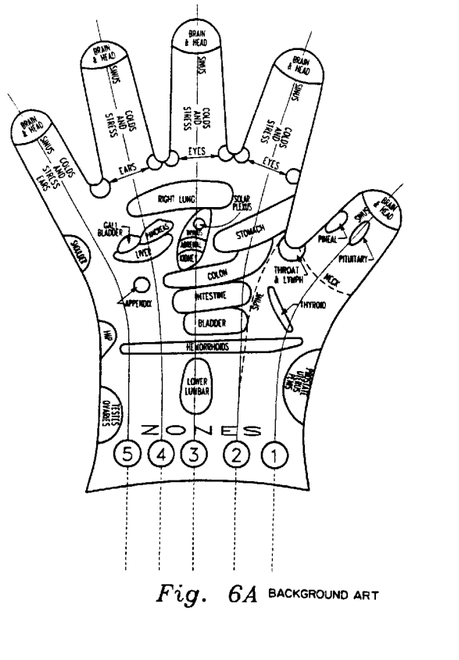
FIGS. 6A and 6B show background art of the reflexology points along with meridians on limbs of an organism such as the hands of a human body.
Figure 6B:
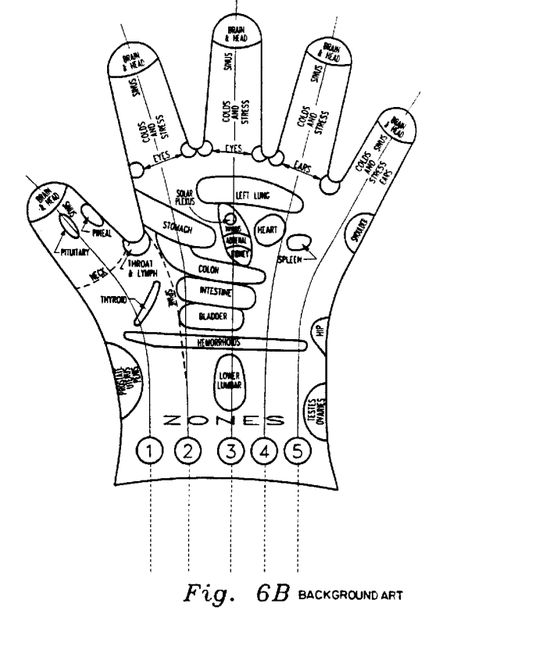

U.S. Pat. No. 5,199,876 to Waldman provides teachings of hand reflexology which is the process of directly stimulating the reflex points in the limb of an organism such as the hand of a human body, the reflex points directly correspond to an organism's internal organs and functions. The Waldman patent explains how an organism such as the human body is divided into ten areas of jurisdiction (meridians), where each area contains its corresponding organs with a reflex counterpart in the hand. An organism such as a human body is shown in FIG. 5 of the present specification, the figure being derived from the Waldman patent. FIG. 5 illustrates the contiguous reflex area lines called meridians contained within a human body. FIGS. 6A and 6B of the present specification, which are also derived from the Waldman patent, provide morphological area maps which identify naturally occurring organ reflex receptor area points or areas in a hand of a human body. FIGS. 6A and 6B further provide approximate locations of the reflex area lines or meridians labeled 1, 2, 3, 4, and 5 which correspond to the reflex area lines or meridians shown in FIG. 5 of the present specification.

In addition to the electromagnetic and bioelectric therapies described with respect to kinesiology and reflexology, the inventor has investigated other areas of alternative medicine encompassing the "subtle energy" system that relates to the mental, emotional, and spiritual self, such an energy system being supported by theories in modern subatomic physics. The energy-oriented therapies, which are founded on the free flow of energy as promoting good health, investigated by the inventor include color/light therapy, which affects physical well-being as well as mood, and electrocrystal therapy, which rectify imbalances in energy flow and thereby reducing energy congestion and disharmony. Further, the inventor investigated and conducted experiments using precepts of healing methods, the wisdom and knowledge of ancient civilizations, particularly Egyptian and Greek, as well as adaptive and innovative extrapolations thereof, such healing methods and wisdom having been often unappreciated, neglected and/or forgotten by modern mankind which concluded that better more modern healing results could be achieved through the application of different or more up-to-date scientific knowledge and technology.

The invention arose from the inventor's appreciation that, while ancient civilizations and societies were constrained by environmental factors including the contemporarily existing state of scientific understanding and development, each civilization attempted evaluation and analysis to explain and understand nature with its repetitive events, physical occurrences and maladies or events affecting the civilization and its people. In this attempt to find order and predictability, not only were theories developed to understand the regularity of the environment but human behavior in ancient civilizations was adapted to be in harmony with such theories. The inventor has determined that the healing approaches of the ancient civilizations were often based on achieving harmony between the ailing person and the nature surrounding them. Thus, the inventor appreciates that one cannot slavishly adhere to any contemporary tenet which which assumes that science and science-based disciplines are the only valid instruments for arriving at objective truth.

An example of a discipline which the modern day established scientific community has often looked upon with suspicion as an unscientific tool of mystics and astrologers is numerology. However, in ancient Egyptian and Greek civilizations, numerology was an analytical technique for the purpose of gaining a deeper knowledge of the patterns of life. One of numerology's basic beliefs or tenets is that the world is alive with vibrating energy, and everything within the world also vibrates with that energy. To the Pythagoreans, the number five (5) was the first universal number, the number of universal love, it being comprised of the first male number three (3) and the first female number two (2). The number 5 represented the incorporation of the principles of polarity and reconciliation. From the roots of 2, 3 and 5, all harmonic proportions and relationships were derived. Regardless of the scientific disdain for numerology, it has its place as an analytic technique for harmonization of organisms with their environment.

The foundations of bioelectric therapy, electromagnetic therapy, electrocrystal therapy and color/light therapy are posited upon all living organisms being formed from atoms or particles, each of which carries energy, and which together form substances through association with one another by the action of an electrical force thereon. In support of the "vibration" tenet of numerology, modern physics has provided insight into the inherent vibration of the living building blocks of nature—the oscillating or vibrating nature of nuclei, atoms and cells. These building blocks as well as the large structures of which they are parts have a natural resonance—an easy and natural way of being. On the other hand, all structures, in addition to having a harmonious natural resonant frequency, can vibrate at dissonant frequencies. It is this nature of movement of energy which gives rise to harmonious or disharmonious, to the positive and negative aspects of health and environment.

With respect to electrocrystal therapy, a crystal is a form of solid matter in which virtually all the atoms and molecules are ordered and structured—a naturally harmonious form. Such crystals can act as crystal frequency generators when an electric potential is applied to them. Thus, when a crystal is placed adjacent to other forms of matter, particularly living matter, and an electric potential is applied to it, the crystal can create harmonious resonance in sub-atomic vibration of neighboring living matter.

With respect of color/light therapy, it is recognized that light energy received by an organism affects the energy as well as chemical balance of the organism. Thus, through use of color, an organism's cells may be brought into energy balance thereby stimulating improved health. In his research, the inventor has determined that the color yellow promotes energy balance. Further, the inventor has determined that use of such color/light therapy in conjunction with electromagnetic, bioelectric and electrocrystal therapy produces an enhancement in the promotion of energy flow in an organism.

Accordingly, the inventor has developed a method and device which promotes energy flow in specific organs, glands, or systems within an organism through the synergistic combination of the numerology, electromagnetic therapy, bioelectric therapy and electrocrystal therapy and color/light therapy.

SUMMARY OF THE INVENTION

Accordingly, it is a primary object of the present invention to provide a method and device for promoting energy flow in an organism which does require little, if any, mechanical manipulation of reflex points or meridian termini of an organism.

It is a further object of the present invention to provide a method and device, a bioenergy channelizer device, for promoting healthy energy flow in an organism which can flank an organism or be located proximate to the organism for transmission of energy to, from and/or through specific organs, glands, or systems within the organism.

It is a further object of the present invention to provide a physically non-intrusive method and device that promotes healthy energy flow within the organism.

It is a further object of the present invention to provide method and device which promotes healthy energy flow about an organism by substantially reducing energy imbalances (deficient or excess energy) which occur between reflex points along or in the vicinity of the meridians in an organism.

Another object of the present invention is to promote healthy flow of energy along or in the vicinity of energy channels or meridians in the organism and the balancing of energy along meridians and/or across meridians or in the vicinity of meridians, such flow being dependent upon the location of the bioenergy channelizer device.

These and other objects of the present invention are fulfilled by providing a device for promoting energy flow in an organism comprising: a first structure having an upper surface with a primary recess portion therein, the primary recess portion having a receiving surface; a second structure having a plurality of arms and a first surface, the second structure being inset into the primary recess portion such that the first surface faces toward the receiving surface; and at least one bioenergy channelizer unit, the at least one bioenergy channelizer unit including: a dielectric material and a plurality of conductive elements, the conductive elements being disposed on the dielectric material in a predetermined spatial relationship, a first conductive element of the conductive elements channelizing energy from a first reflex point in the vicinity of a first meridian in the organism, the first conductive element transmitting the energy received in the vicinity of the first reflex point to a second conductive element of the conductive elements, the second conductive element transmitting the received energy from the first reflex point toward a second reflex point in the vicinity of at least one of the first and a second meridian in the organism, whereby healthy flow of energy within the organism is substantially increased, wherein one of the at least one bioenergy channelizer unit is positioned adjacent the primary recess portion.

In addition, these and other objects of the present invention are also accomplished by providing a method for promoting energy flow in an organism comprising the steps of: providing a bioenergy channelizer device, the device including: a first structure having an upper surface with a primary recess portion therein, the primary recess portion having a receiving surface; a second structure having a plurality of arms and a first surface, the metal structure being inset into the primary recess portion such that the first surface faces toward the receiving surface; and at least one bioenergy channelizer unit, the at least one bioenergy channelizer unit including: a dielectric material and a plurality of conductive elements, the conductive elements being disposed on the dielectric material in a predetermined spatial relationship, and at least one bioenergy channelizer unit being positioned adjacent the primary recess portion; flanking the organism with the bioenergy channelizing device; channelizing energy with the conductive elements from a first reflex point in the vicinity of a first meridian of the organism; and transmitting energy channelized from the first reflex point with the conductive elements toward a second reflex point in the vicinity of at least one of the first meridian and a second meridian of the organism, whereby healthy flow of energy within the organism is substantially increased.

Further, these and other objects of the present invention are also accomplished by providing a method for promoting energy flow in an organism comprising the steps of: providing a bioenergy channelizing device, the providing step including: forming a first structure having an upper surface with a primary recess portion therein including a receiving surface; forming a metallic ankh using a water jet cutter, the ankh including a first surface, a longitudinal piece and a crosspiece; insetting the metallic ankh into the primary recess portion such that the first surface faces the receiving surface; flanking the organism with the bioenergy channelizing device; channelizing energy with the metallic ankh from a first reflex point in the vicinity of a first meridian of the organism; and transmitting energy channelized from the first reflex point with the metallic ankh toward a second reflex point in the vicinity of at least one of the first meridian and a second meridian of the organism, whereby healthy flow of energy within the organism is substantially increased.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein.

DETAILED DESCRIPTION OF THE PREFERRED EMBODIMENTS

Figure 1:
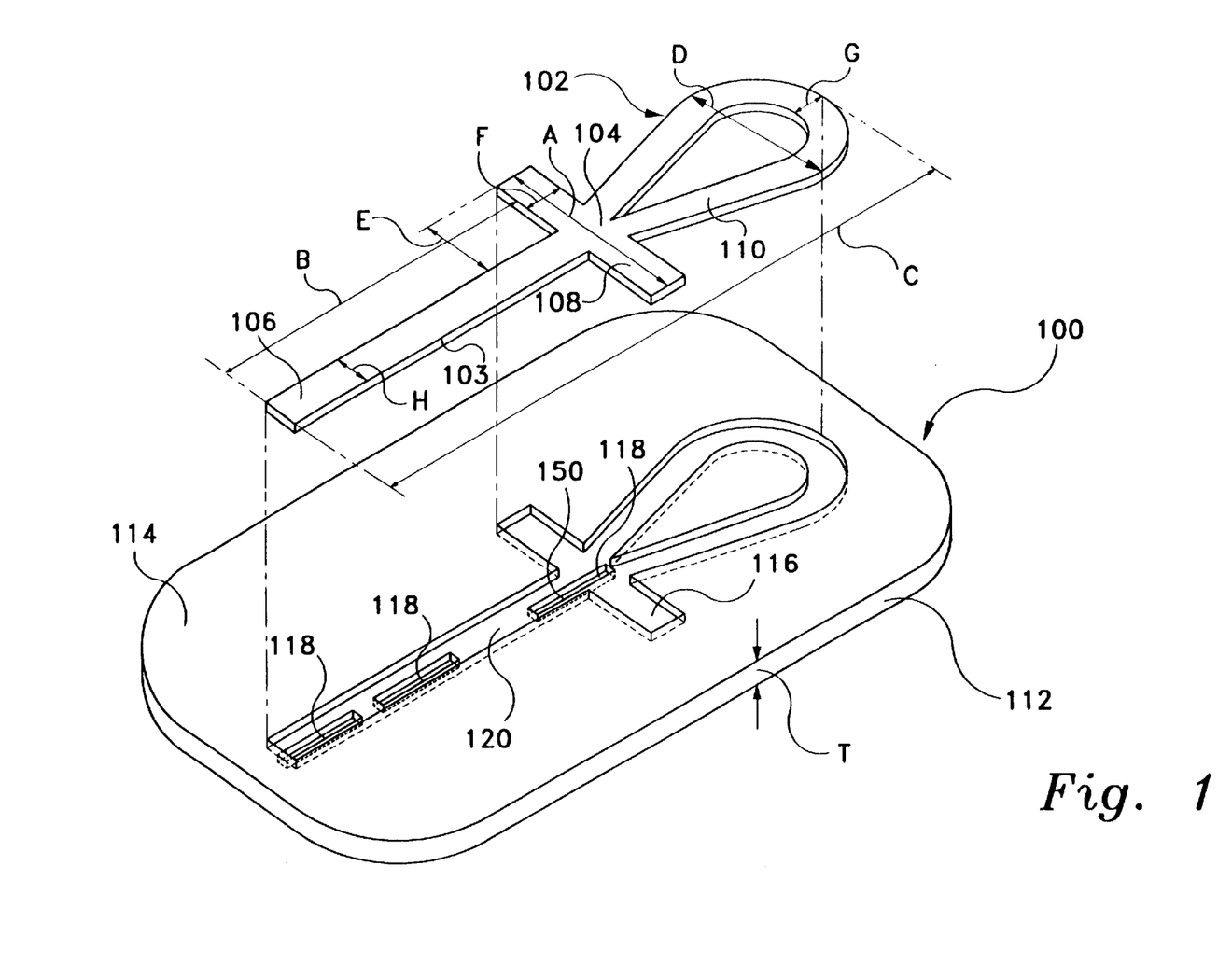
FIG. 1 is an exploded perspective view of the inventive bioenergy channelizer device.

Referring to FIG. 1, a device for promoting energy flow, or a bioenergy channelizer device 100, is shown. The bioenergy channelizer device promotes energy flow in an organism by receiving energy from the organism and retransmitting this received energy back to the organism. (However, additionally, it is noted that movement of a below described device through an electrical, magnetic, electromagnetic or other energy field may cause energy flow along the device.) The bioenergy channelizer device is preferably used on an organism such as the human body, but other organisms such as animals, plants or other living organisms are not beyond the scope of the present invention. The bioenergy channelizer devices 100 relates to energy which propagates through an organism which is synonymous with Qi (pronounced chi) of Chinese acupuncture, and with Prana of traditional Indian medicine and philosophy, and energy associated with the universal life-force present in an organism. The energy discussed herein also relates to the energy which is associated with kinesiology and reflexology.

The bioenergy channelizer device 100 "channelizes" or "harnesses" energy emitted from an organism and surrounding an organism, such energy taking many forms. Such forms of energy include, but are not limited to, electromagnetic energy, magnetic energy in the form of magnetic fields, biochemical energy, thermal energy, and light energy, or other like energy forms.

The bioenergy channelizer unit 100 is preferably designed to receive and transmit energy that flows in the vicinity of the meridians or energy channels of a living organism. It is contemplated that one or more of the components of the bioenergy channelizer device 100 receive energy from one reflex point in the vicinity of one meridian and transmits energy to another reflex point in the vicinity of that or another meridian. However, the bioenergy channelizer device 100 can receive energy from along a single meridian and retransmit energy to the same meridian from which the energy was received. The bioenergy channelizer device 100 can receive energy from at least one reflex point with respect to at least one meridian and transmit this received energy to one or more reflex points at one or more meridians. Alternatively, the bioenergy channelizer device 100 can receive energy from the vicinity of one meridian and retransmit the received energy to the vicinity of a plurality of meridians within a living organism.

The bioenergy channelizer device 100 comprises a metallic structure 102 having a central portion 104 and a plurality of arms extending therefrom, specifically a longitudinal piece 106 and a crosspiece 108 which together form a cross structure. The generally flat metallic structure 102 has a thickness of approximately 1.5 mm and is composed with an electrically conductive element such as copper, aluminum, gold, silver, an alloy thereon, and a ceramic material, but preferably copper or a copper alloy. The longitudinal piece 106 is greater in length than the crosspiece 108 with the cross preferably being an Egyptian cross or ankh, such that one end of the cross is in a rounded, inverted teardrop form 110. While the metallic structure 102, particularly in the form of an ankh may be formed by a variety of manufacturing or forming methods and techniques, to include, but not limited to, casting, pressing, forging, and cutting, the inventor has found that forming such structure by water jet cutting provides overall improved promotion of energy flow.

Through experimentation and investigation, the inventor has determined preferable approximate dimensions for the metallic structure 102 having an ankh form. From study, the inventor has determined that healthy energy flow within an organism is promoted and increased by forming the metallic ankh with the dimensions for A, B and C generally according to the harmony relationships as exemplified in the basic proportionality laws such as the Golden Section number Phi, namely in the relationship such that the C minus B=A times $\Phi$ plus or minus 5%, where $\Phi$=Phi=1.618.

Through investigation, the inventor has determined that the metallic structure 102, in conjunction with the at least one mineral crystal 150, described hereinbelow, and/or at least one bioenergy channelizer unit 20, described hereinbelow, can be quite beneficial in promoting and increasing the healthy flow of energy in an organism. However, recognizing that the combination of the components of device 100 can produce a high gauss, such that promotion and increase of energy flow can pass a threshold beyond which the benefits-to-cost ratio for promoting and increasing healthy flow of energy begins to decline, the inventor has developed preferable dimensions, though by no means the exclusive example for the dimensions, for the metallic structure 102. As a result, the A, B, and C dimensions of the metallic structure 102 have been particularly identified for an adult human being of generally average mass and average weight with the dimensions set forth below, with the dimensions being identified in FIG. 1.

A: Overall length of the crosspiece 108=14.0 cm

B: Section length of non-ankh portion of longitudinal piece 106=29.0 cm

C: Overall length of the longitudinal piece 106=52.0 cm

D: Width of ankh portion of longitudinal piece 106=13.8 cm

E: Length of crosspiece 108 extending beyond longitudinal piece 106=5.6 cm

F: Width of crosspiece 108=2.8 cm

G: Width of ankh portion of longitudinal piece 106=2.8 cm

H: Width of non-ankh portion of longitudinal piece 106=2.8 cm

The above dimensions were determined with deference to the Golden Section number Phi by which ©–B)=22.652, or rounded, 23.

Further, as can be seen above, following from the previously mentioned Pythagorean numerology, particularly the use of the first numbers of 5, 2, and 3, the inventor determined that the value of A should be set as A=(5×F), the value of E=(2×F), and the value of B={[(2×F)+$\Phi$]}×2$\Phi$. Thus, B=29.35, or rounded, 29.

In addition, it is within the scope of this invention that, for a living organism above or below the above dimensions for an average size human, the lengths and widths of the metallic structure 102 may be increased or decreased, for example, proportionally.

The bioenergy channelizer 100 device further comprises a three-dimensional structure 112 with the corners joining its width dimensions to its length dimensions being rounded such that an arc connects the adjacent pairs of sides. The structure 112 is preferably formed, at least partially, from wood, preferably a softwood, more preferably, a conifer wood, most preferably spruce; and has a thickness T of 1.5 cm to 2.3 cm, preferably 2.0 cm. The wooden structure 112 can be formed from either a single piece of wood or multiple pieces of wood, preferably three pieces. In a generally rectangularly shaped upper surface 114 of the wooden structure 112 is formed a primary recess portion 116. At least one secondary recess portion 118 is formed in a receiving surface 120 of the primary recess portion 116. Further, it is within the scope of the invention to form at least one secondary recess portion 118 in the wooden structure 112 adjacent to the receiving surface 120, but not contiguous therewith. The secondary recess portions 118 are located along the longitudinal piece 106 at the intersection of the longitudinal piece 106 and the crosspiece 108, at a distal end of the longitudinal piece of the non-ankh portion, and a position therebetween. Preferably, the portions 118 are formed in the receiving surface 120 of the primary recess portion. The receiving surface 120 receives the metallic structure 102 which is inset thereinto with a first surface of the metallic structure 102 facing toward the receiving surface 120, the longitudinal piece 106 of the metallic structure 102 extending substantially along the longitudinal axis of the wooden structure 112. However, it is within the scope of the invention that longitudinal piece 106 extends at an angle to such longitudinal axis.

The relative length and width dimensions of the wooden structure 112 should be sufficient length to accommodate the metallic structure within the bounds of the upper surface. In this regard, the inventor has determined that a ratio of length to width of the wooden structure 112 is 3 to 2. However, it is within the scope of the invention that such a ratio may vary and that an end or ends of the either of the longitudinal piece and the crosspiece extend outward from the edges of the wooden structure. For that matter, it is within the scope of the invention that at least a portion of the primary recess portion 116 extends through the wooden structure from upper surface to lower surface.

The bioenergy channelizer device 100 further comprises at least one mineral crystal acting as an energy resonator to receive, amplify and re-transmit energy. Several types of powerful mineral crystals are red jasper, amethyst, malachite, quartz and lapis lazuli, with the preferable mineral crystal being lapis lazuli, especially lapis lazuli from deposits in and around present day Afghanistan. It is not beyond the scope of the invention that the mineral crystals may be in pulverized form. Further, it is not beyond the scope of the invention that the at least one mineral crystal is man-made rather than naturally occurring. The at least one mineral crystal is disposed in a secondary recess portion 118. Following experimentation, the inventor determined that it is preferable that the at least one mineral crystal be disposed in the secondary recess portion 118 located adjacent the intersection of the longitudinal piece 106 and the crosspiece 108.

Figure 2A:
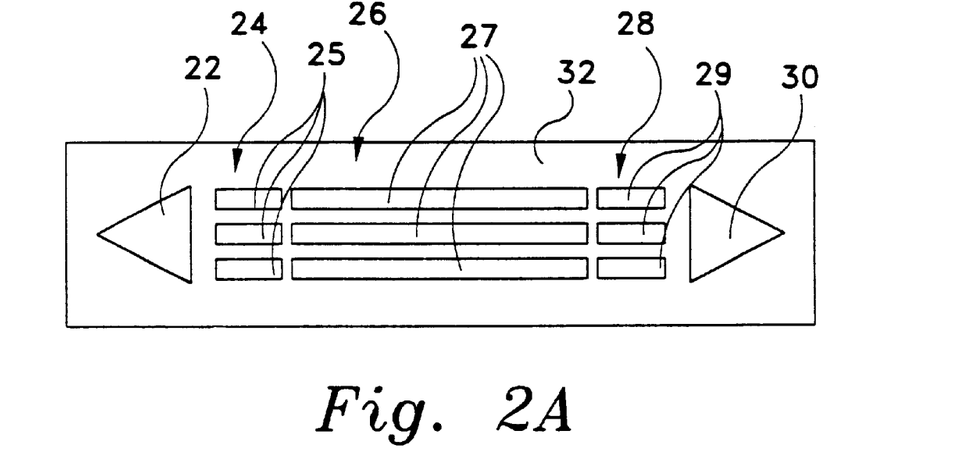
FIG. 2A is an elevational view of the bioenergy channelizer unit of the present invention.

The bioenergy channelizer device 100 further comprised at least one bioenergy channelizer unit 20. Referring to FIG. 2A, a unit for promoting energy flow, or a bioenergy channelizer unit 20, is shown. The bioenergy channelizer unit promotes energy flow in an organism by receiving energy from the organism and retransmitting this received energy back to the organism. (However, additionally, it is noted that movement of a unit through an electrical, magnetic, electromagnetic or other energy field may cause energy flow along the unit.) The bioenergy channelizer unit 20 relates to energy which propagates through an organism which is synonymous with Qi (pronounced chi) of Chinese acupuncture, and with Prana of traditional Indian medicine and philosophy, and energy associated with the universal life-force present in an organism. The energy discussed herein also relates to the energy which is associated with kinesiology and reflexology.

The bioenergy channelizer unit 20 "channelizes" or "harnesses" energy emitted from an organism and surrounding an organism, such energy taking many forms. Such forms of energy include, but are not limited to, electromagnetic energy, magnetic energy in the form of magnetic fields, biochemical energy, thermal energy, and light energy, or other like energy forms.

The bioenergy channelizer unit 20 is preferably designed to receive and to transmit energy that flows within the meridians or energy channels of a living organism. It is contemplated that the bioenergy channelizer unit 20 receives energy from one reflex point in the vicinity of one meridian and transmits energy to another reflex point in the vicinity of that or another meridian. However, the bioenergy channelizer unit 20 can receive energy from along a single meridian and retransmit energy to the same meridian from which the energy was received. The bioenergy channelizer unit 20 can receive energy from at least one reflex point with respect to at least one meridian and transmit this received energy to one or more reflex points at one or more meridians. Alternatively, the bioenergy channelizer unit 20 can receive energy from the vicinity of one meridian and retransmit the received energy to the vicinity of a plurality of meridians within a living organism.

The bioenergy channelizer unit 20 preferably includes a plurality of conductive elements 22, 24, 26, 28, and 30. The conductive elements 22, 24, 26, 28, and 30 are preferably made from silver but other conductive materials forming one or more of the elements are not beyond the scope of the present invention. Other materials include but are not limited to other precious metals such as gold, but include copper, stainless steel, various alloys, nonferrous alloys, nonferrous materials, ceramic materials and other conductive materials which promote energy flow within an organism. It is contemplated that when energy is emitted from an organism in the form of a magnetic field, at least one of the conductive elements 22, 24, 26, 28, and 30 will move relative to the lines of force of such a magnetic field to promote or induce an electric current therein. However, as stated above, the energy forms propagating through an organism can include, but are not limited to, electromagnetic energy, magnetic energy, electrical energy, chemical energy, thermal energy, and other like energy forms.

In the preferred embodiment of the bioenergy channelizer unit 20 as shown in FIG. 2A, the bioenergy channelizer unit 20 includes a first conductive element 22 which has a predetermined geometrical shape. In the preferred embodiment, the preferred geometrical shape of the first conductive element 22 is a triangle. However, other shapes of the first conductive element are not beyond the scope of the present invention. Other shapes include but are not limited to circular, elliptical, square, rectangular, pentagonal, hexagonal, octagonal, and other polygonal shapes. While only a single conductive element 22 is shown in FIG. 2A, a plurality of conductive portions which are grouped in the shape of a triangle is not beyond the scope of the present invention. In other words, a plurality of conductive sub-parts which form a triangular perimeter could also be employed as the first conductive element 22. As to dimensions of the preferred triangular shaped embodiment of the first conductive element 22, through study and experimentation, the inventor has determined that the ratio of the distance from the distal point of the structure to the base width of the structure is less than 1, preferably in a ratio of 7/10, and more preferably 11/15.

A second conductive element 24 preferably includes a plurality of conductive portions 25. Each of these second conductive portions 25 preferably has a rectangular shape however, similar to the first element 22, other shapes are not beyond the scope of the present invention. Other shapes include but are not limited to elliptical, circular, square, trapezoidal, pentagonal, hexagonal, octagonal and other like polygonal forms. Each of the second conductive portions 25 includes a surface area which is equivalent with respect to a neighboring conductive portion 25 of the plurality. While portions 25 of the second conductive element 24 are shown, it is not beyond the scope of the present invention to form the second conductive element 24 as a single conductive portion.

The conductive portions 25 are preferably aligned in a parallel manner adjacent to the first conductive element 22. The second conductive portions 25 preferably include first sides and second sides where the first sides are substantially larger than the second sides. The second smaller sides are preferably aligned in a parallel manner with respect to one side of the first conductive element 22 which is typically triangularly shaped. The second conductive portions 25 are spaced from the conductive element 22 according to a predetermined distance which facilitates energy flow between conductive elements and a living organism.

The third conductive element 26 includes a plurality of conductive portions 27 which are spaced apart from the second conductive portions 25 by a predetermined distance which facilitates energy flow between the conductive elements/portions and a living organism. Similar to the second conductive portions 25, the third conductive portions 27 preferably include a rectangular shape. However, each third conductive portion 27 preferably includes surface areas which are substantially larger than the surface areas of the second conductive portions 25. While the conductive portions 27 are preferably rectangular in shape, other shapes of the third conductive portions 27 include but are not limited to circular, elliptical, square, pentagonal, hexagonal, octagonal and other polygonal shapes.

The third conductive portions 27 are preferably substantially aligned in a parallel manner and include first sides and second sides. Each first side of each third rectangular conductive portion 27 is substantially larger than each second side of each third conductive portion 27. The second sides of the third conductive portions 27 are substantially aligned in a parallel manner with respect to the second sides of the second conductive portions 25.

The third conductive portions 27 are spaced apart from each other for a predetermined distance and are spaced apart from the second conductive portions 25 by a predetermined distance which substantially promotes energy flow between the conductive elements in addition to energy flow between the conductive elements and the organism. Similar to the second conductive portions 25, the third conductive portions 27 can include a single conductive portion formed in a unitary structure or can include additional conductive portions which form a substantially similar shape of the plurality of third conductive portions 27 shown in FIG. 2A. In other words, a single conductive portion can replace the three conductive portions 27 shown in FIG. 2A or the third conductive element 26 can include 4, 5, or 6 separate portions or multiples of three conductive elements such as 6, 9, and 12, instead of the three conductive portions 27 shown.

The fourth conductive element 28 includes a plurality of conductive portions 29 which are substantially similar to the second conductive portions 25. Therefore, since the third conductive portions 29 are substantially similar to the second conductive portions 25, a description of the fourth conductive portions 29 is not necessary.

Similar to the fourth conductive portions 29 relative to the second conductive portions, the fifth conductive element 30 is substantially similar in structure to the first conductive element 22. The fifth conductive element 30 can include alternate embodiments similar to those discussed with reference to the first conductive element 22 where multiple portions form the fifth conductive element 30. Additionally, the previously noted ratio dimensions of the first conductive element 22 are applicable to the fifth conductive element. Accordingly, further discussion of the fifth conductive element 30 is not necessary.

Viewing the bioenergy channelizer unit as a whole, the symmetry of the whole unit 20, is apparent to an observer. The first triangular conductive element 22 "points" or is directed in a first direction while the fifth triangular conductive element 30 "points" or is oriented in a second direction which is substantially 180° relative to the first direction of the first conductive element 22. The symmetry of the bioenergy channelizer unit 20 is further emphasized by the second conductive element 24 which is disposed between the first conductive element 22 and the second conductive 26 while the fourth conductive element 28 is disposed between the third conductive element 26 and the fifth conductive element 30. It is believed that the relative spacing between the elements (within a specified group such as the spacing between respective portions 25) in addition to the relative spacing between adjacent conducting elements (such as elements 24 and 26) and the spacing of the conductive elements 22, 24, 26, 28, and 30 with respect to an organism promote energy flow from the living organism to the conductive elements 22, 24, 26, 28, and 30 and back to the living organism. The conductive elements 22, 24, 26, 28, and 30 are preferably disposed upon a dielectric layer 32.

FIG. 2A shows the bioenergy channelizer unit 20 without first or second covering layers 34 and 42 or dielectric layers 32 and 40. The first covering layer 34 is preferably a dielectric material. The dielectric material is preferably leather, Gore-Tex™, Altacara, or Silon (preferably with microcapsules of etheric oils contained within its structure), but other types of dielectric materials are not beyond the scope of the present invention. Other types of materials include but are not limited to silicon, polyethylene, Teflon™, polystyrene, polyvinyl chloride, nylon, rubber epoxy, paraffin wax, fused silica and water and other like dielectric materials.

Figure 2B:
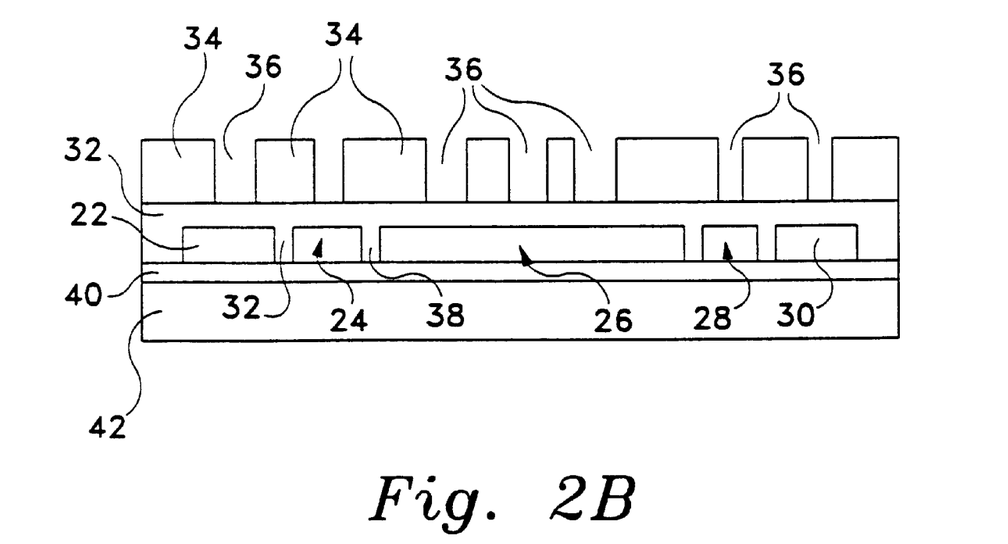
FIG. 2B is a cross-sectional view of the bioenergy channelizer unit of the present invention.

As seen in FIG. 2B which shows a complete cross section of the bioenergy channelizer unit 20 along with the covering layer 34 which includes a plurality of apertures 36 which penetrate completely through the first covering layer 34 to expose surfaces of the first dielectric material layer 32. The apertures 36 are preferably circular in shape, but other shapes are not beyond the scope of the present invention. Other shapes of the apertures 36 include but are not limited to elliptical, square, rectangular, pentagonal, hexagonal, octagonal and other like polygonal shapes. The apertures preferably have a maximum diameter of 1 mm. However, other sizes are not beyond the scope of the present invention. However, dependent on the use of materials for first covering layer 34 and/or anticipated utilization of the bioenergy channelizer unit 20 on the organism, the apertures 36 are optional such that the first covering layer 34 has no formed apertures which penetrate completely through the layer.

Between the conductive elements 22, 24, 26, 28, and 30, the first dielectric material layer 32 is preferably disposed. However, it is possible to form the bioenergy channelizer unit where an absence of material or lack of material is present between the respective conductive elements 22, 24, 26, 28, and 30. For example, the spaces or pockets 38 can be filled with atmospheric air or a vacuum. The conductive elements 22, 24, 26, 28, and 30, are further disposed upon a second dielectric layer 40 which is preferably silicon. However, other types of dielectric materials are not beyond the present invention and include but are not limited to leather, polyethylene, Teflon™, polystyrene, polyvinyl chloride, nylon, rubber epoxy, paraffin wax, fused silica and water and other like dielectric materials. Furthermore, it is not beyond the scope of the present invention where the first dielectric layer 32 and second dielectric layer 40 are essentially one dielectric layer which encapsulate the conductive elements 22, 24, 26, 28, and 30. Such an embodiment where the dielectric layers 32 and 40 are a unitary structure would facilitate efficient manufacturing of the bioenergy channelizer unit 20.

The thickness of the first dielectric 32 and the second dielectric layer 40 are dependent upon the amount of energy emitted from the living organism in which the bioenergy channelizer unit 20 is attached thereto. Therefore, the thicknesses of the dielectric layers can vary depending upon the strength of the energy being emitted from, or to be directed to, the living organism. It is contemplated that the spacings between the conductive elements 22, 24, 26, 28, and 30 and the thickness of the dielectric layers 32 and 40 are dependent upon the particular energy field of an organism where each living organism may include different energy field strengths with respect to a similar living organism.

The second dielectric layer 40 may also be spaced between the conductive elements 22, 24, 26, 28, and 30, in addition to the dielectric layer 32, and a second covering layer 42. The second covering layer 42 is preferably made of a dielectric material similar to the material of the first covering layer 34 (leather, Gore-Tex™, or Altacara). While the second covering layer 42 has a thickness which is dependent upon the amount of energy being emitted from, or directed to, the living organism, the thickness of the second covering layer 42 is also dependent upon the intended environment of the bioenergy channelizer unit 20.

For example, when the bioenergy channelizer unit 20 is used in conjunction with the metallic structure 102 and/or one or more mineral crystals 150 of the device 100. The thickness of either of the first covering layer 34 or the second covering layer 42 may depend upon other materials that lie adjacent to the second covering material such as the structure and consistency of the metallic structure 102 and the wooden structure 112. In fact, investigations have shown that, due to the rigidity of the metallic structure 102 and the wooden structure 112, a unit 20, used in conjunction with the metallic structure 102 and/or the mineral crystal 150 as an insert in a secondary recess portion 118, requires neither of the first covering layer 34 nor the second covering layer 42, and requires only requiring one of the first dielectric layer 32 and the second dielectric layer 40.

The thicknesses and the relative spacings between the conductive elements 22, 24, 26, 28, and 30 with respect to the living organism and the surrounding dielectric layers 32 and 40 and the covering layers 34 and 42 can be varied in accordance with the desired amount of energy interaction that is desired to occur between the bioenergy channelizer unit 20, and/or the device 100, and the organism.

When used in conjunction with the metallic structure 102, at least one unit 20 may be disposed inside any one of the secondary recess portions 118. A unit 20 having the conductive elements mounted on a dielectric layer, with no covering layer 34 or 42 present, is disposed in the secondary recess portion 118 adjacent to the intersection of the longitudinal piece 106 and crosspiece 108, the dielectric layer is preferably interposed between the metallic structure 102 and the conductive elements. Further, when at least one mineral crystal is disposed within such secondary recess portion, the crystal(s) is interposed between the dielectric layer and the metallic structure 102. However, it is within the scope of the invention that the at least one mineral crystal and such unit 20 may be disposed in other configurations within such secondary recess portion 118. A similarly constructed unit 20 may be disposed in a secondary recess portion 118 other than that adjacent to the intersection of the longitudinal piece 106 and crosspiece 108, having the conductive elements mounted on a dielectric layer, with no covering layer 34 or 42. In such case, the conductive elements of such unit 20 are preferably interposed between the metallic structure 102 and the dielectric layer. However, it is within the scope of the invention that the at least one mineral crystal and such unit 20 may be disposed in other configurations within such secondary recess.

Furthermore, the bioenergy channelizer device 100 comprises a plastic covering (not shown) which surrounds the above identified elements when they are assembled. The plastic covering is generally 2 to 3 mm thick and preferably encloses the entire wooden structure 112 with the metallic structure 102 inset therein. The plastic covering contains a yellow pigment. The plastic covering must be durable but yet pliable. It has been found that a plastic material formed from organic synthetic or processed materials that include polymers, particularly thermoplastic or thermosetting polymers, reinforced with fiberglass satisfies both conditions. In particular, it has been found that a combination of the plastic material Colpoly 720 and fiberglass provide a notably suitable covering.

The method for promoting energy flow in an organism includes providing a bioenergy channelizer device 100 to flank the organism 1. The method provides a bioenergy channelizer device 100, the device including: a first structure 112 having an upper surface 114 with a primary recess portion 116 therein, the primary recess portion having a receiving surface 120; a second structure 102 having a plurality of arms 106, 108 and a first surface 103, the metal structure 102 being inset into the primary recess portion 116 such that the first surface 103 faces toward the receiving surface 120; and at least one bioenergy channelizer unit 20, the at least one bioenergy channelizer unit including: a dielectric material 32 and a plurality of conductive elements 22, 24, 26, 28 and 30, the conductive elements being disposed on the dielectric material 32 in a predetermined spatial relationship, and the at least one bioenergy channelizer unit 20 being positioned adjacent the primary recess portion 116. Next, the method requires flanking the organism with the bioenergy channelizing device 100, channelizing energy with the conductive elements 22, 24, 26, 28, and 30 from a first reflex point in the vicinity of a first meridian of the organism. The received or channelized energy is then transmitted from the first reflex point with the conductive elements 22, 24, 26, 28, and 30 toward a second reflex point in the vicinity of at least one of the first meridian and a second meridian of the organism, whereby healthy flow of energy within the organism is substantially increased.

Another method for promoting energy flow in an organism includes providing a bioenergy channelizer device 100 to flank the organism 1. The method provides a bioenergy channelizing device, the providing step including: forming a first structure 112 having an upper surface 114 with a primary recess portion 116 therein including a receiving surface 120; forming a metallic ankh 102 using a water jet cutter, the ankh including a first surface 103, a longitudinal piece 106 and a crosspiece 108; and insetting the metallic ankh into the primary recess portion 116 such that the first surface 103 faces toward the receiving surface 120. The method further includes the step of flanking the organism with the bioenergy channelizing device; channelizing energy with the metallic ankh from a first reflex point in the vicinity of a first meridian of the organism; and transmitting energy channelized from the first reflex point with the metallic ankh 102 toward a second reflex point in the vicinity of at least one of the first meridian and a second meridian of the organism, whereby healthy flow of energy within the organism is substantially increased. Such method further includes the step of forming at least one bioenergy channelizer unit 20 by placing conductive elements 22, 24, 26, 28, and 30 on a dielectric material 32 in a predetermined spatial relationship, the step of forming at least one secondary recess portion 118 in one of the receiving surface 120 and the first surface 103, the step of positioning at least one bioenergy channelizer unit 20 inside at least one of the at least one secondary recess portion, channelizing energy with the conductive elements 22, 24, 26, 28, and 30 from a first reflex point in the vicinity of a first meridian of the organism. The received or channelized energy is then transmitted from the first reflex point with the conductive elements 22, 24, 26, 28, and 30 toward a second reflex point in the vicinity of at least one of the first meridian and a second meridian of the organism, whereby healthy flow of energy within the organism is substantially increased.

The method further includes enhancing the steps of channelizing energy and transmitting energy using at least one mineral crystal 150 and a plastic covering around the structures 102 and 112, the covering containing a yellow color pigment.

In application of the bioenergy channelizer device and method of its use for the promotion of healthy energy flow in an organism, proportionality is of practical importance. While preferable dimensions have been set forth, the size of the device can be increased or decreased dependent upon the organism or the portion thereof with which it is to be used. Alternatively, the size of the device can depend on the distance by which the device is separated from the organism which it flanks, for example, the device being placed under a flexible support, such as mattress, upon which an organism reclines. Lastly, the number of components such as the bioenergy channelizer units and/or number and type of mineral crystals incorporated in the device may affect its size to obtain optimum beneficial use in promoting healthy energy flow in, to, from or through specific organs, glands, or systems within the organism when the device is flanked or placed adjacent such organism in the vicinity of, reflex points or meridian termini.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What I claim is:

1. A device for promoting energy flow in an organism comprising:
   a first structure having an upper surface with a primary recess portion therein, said primary recess portion having a receiving surface,
   a second structure having a plurality of arms and a first surface, said second structure being inset into said primary recess portion such that said first surface faces said receiving surface, and
   at least one bioenergy channelizer unit, said at least one bioenergy channelizer unit including:
      a dielectric material; and
      a plurality of conductive elements; said conductive elements being disposed on the dielectric material in a predetermined spatial relationship, a first conductive element of said conductive elements channelizing energy from a first reflex point in the vicinity of a first meridian in the organism, said first conductive element transmitting the energy received in the vicinity of the first reflex point to a second conductive element of said conductive elements, said second conductive element transmitting the received energy from the first reflex point toward a second reflex point in the vicinity of at least one of the first and a second meridian in the organism, whereby healthy flow of energy within the organism is substantially increased,
   wherein one of said at least one bioenergy channelizer unit is positioned adjacent said primary recess portion.

2. The device according to claim 1, wherein said second structure contains copper and is in the form of a cross including a longitudinal piece and a crosspiece.

3. The device according to claim 1, wherein said receiving surface has at least one secondary recess portion therein, and one of said at least one bioenergy channelizer unit is positioned inside at least one of said at least one secondary recess portion.

4. The device of claim 3, wherein one of said at least one secondary recess portion is positioned adjacent the intersection of said longitudinal piece and said crosspiece.

5. The device of claim 3, further comprising at least one mineral crystal, said at least one crystal being positioned inside one of said at least one secondary recess portion.

6. The device of claim 4, further comprising at least one mineral crystal, said at least one crystal being positioned inside said one of said at least one secondary recess portion.

7. The device of claim 5, wherein said mineral crystal includes lapis lazuli.

8. The device of claim 6, wherein said mineral crystal includes lapis lazuli.

9. The device of claim 2, wherein the cross is an ankh.

10. The device of claim 9, wherein the length of said longitudinal piece being greater than the length of said crosspiece and the ratio of the difference between the length of said longitudinal piece and the length of a section of said longitudinal piece extending from the crosspiece to a distal end thereof to the length of the crosspiece is within five percent of the value of the Golden Section number Phi, said Golden Section number Phi equaling 1.618.

11. The device of claim 1, wherein said first structure is formed from a softwood.

12. The device of claim 11, wherein the softwood is spruce.

13. The device of claim 1, further comprising a plastic covering surrounding said first structure and said second structure inset therein.

14. The device of claim 13, wherein said plastic covering contains a yellow color pigment.

15. The device of claim 1, wherein the conductive elements include a first set and a second set of conductive elements, said first set of conductive elements having a first predetermined geometrical shape, and said second set of conductive elements having a second predetermined geometrical shape.

16. The device of claim 15, wherein the first set of conductive elements include triangularly shaped elements, and said second set of conductive elements include quadrangularly shaped elements.

17. The device of claim 1, wherein at least one of the plurality of conductive elements is formed from at least one of silver, gold, copper and ceramic material.

18. The device of claim 11, wherein said first structure includes three parts, said three parts being bound together.

19. The device of claim 3, wherein the number of said at least one secondary recess portion is at least two, one of said secondary recess portion being positioned adjacent a distal portion of said longitudinal piece.

20. The device of claim 4, wherein said one of said at least one secondary recess portion has positioned therein at least one lapis lazuli crystal and one of said at least one bioenergy channelizer unit.

21. A method for promoting energy flow in an organism comprising the steps of:
   providing a bioenergy channelizer device, said device including:
      a first structure having an upper surface with a primary recess portion therein, said primary recess portion having a receiving surface,
      a second structure having a plurality of arms and a first surface, said second structure being inset into said primary recess portion such that said first surface faces toward said receiving surface, and
      at least one bioenergy channelizer unit, said at least one bioenergy channelizer unit including:
         a dielectric material; and
         a plurality of conductive elements; said conductive elements being disposed on the dielectric material in a predetermined spatial relationship, and
      said at least one bioenergy channelizer unit is positioned adjacent said primary recess portion,
   flanking the organism with said bioenergy channelizing device;
   channelizing energy with the conductive elements from a first reflex point in the vicinity of a first meridian of the organism; and transmitting energy channelized from the first reflex point with the conductive elements toward a second reflex point in the vicinity of at least one of the first meridian and a second meridian of the organism, whereby healthy flow of energy within the organism is substantially increased.

22. The method of claim 21, wherein said second structure contains copper and is in the form of a cross including a longitudinal piece and a crosspiece, and wherein said bioenergy channelizer device further includes at least one secondary recess portion formed in at least one of said receiving surface and said first surface.

23. The method of claim 22, wherein one of said at least one secondary recess portion is positioned adjacent the intersection of said longitudinal piece and said crosspiece.

24. The method of claim 22, further comprising at least one mineral crystal, said at least one crystal being positioned inside said one of said at least one secondary recess portion.

25. The method of claim 24, wherein the cross is an ankh.

26. A method for promoting energy flow in an organism comprising the steps of:
   providing a bioenergy channelizing device, said providing step including:
      forming a first structure having an upper surface and a primary recess portion therein including a receiving surface,
      forming a metallic ankh using a water jet cutter, said ankh including a first surface, a longitudinal piece and a crosspiece, and
      insetting said metallic ankh into said primary recess portion such that said first surface faces toward said receiving surface;
   flanking the organism with said bioenergy channelizing device;
   channelizing energy with said metallic ankh from a first reflex point in the vicinity of a first meridian of the organism; and
   transmitting energy channelized from the first reflex point with said metallic ankh toward a second reflex point in the vicinity of at least one of the first meridian and a second meridian of the organism, whereby healthy flow of energy within the organism is substantially increased.

27. The method of claim 26, wherein said providing step further includes the step of:
   forming at least one secondary recess portion in said receiving surface;
   forming at least one bioenergy channelizer unit, said at least one bioenergy channelizer unit including:
      a dielectric material; and
      a plurality of conductive elements; said conductive elements being disposed on the dielectric material in a predetermined spatial relationship, and
further comprising the step of:
   positioning one of said at least one bioenergy channelizer unit inside at least one of said at least one secondary recess portion;
   channelizing energy with the conductive elements from a first reflex point in the vicinity of a first meridian of the organism; and
   transmitting energy channelized from the first reflex point with the conductive elements toward a second reflex point in the vicinity of at least one of the first meridian and a second meridian of the organism, whereby healthy flow of energy within the organism is substantially increased.

28. The method of claim 27, wherein said step of providing further includes the steps of:
   positioning at least one mineral crystal inside one of said at least one secondary recess portion, and
further comprising the step of:
   enhancing the steps of channelizing energy and transmitting energy with said at least one crystal.

29. The method of claim 28, wherein said step of forming said at least one secondary recess portions includes the step of:
   positioning one of said at least one secondary recess portion adjacent the intersection of said longitudinal piece and said crosspiece, and wherein
said step of providing further includes the step of:
   positioning one of said at least one bioenergy channelizer unit and at least one said crystal, said at least one crystal including lapis lazuli, inside said one of said at least one secondary recess portion adjacent the intersection of said longitudinal piece and said crosspiece.

30. The method of claim 28, wherein said step of providing further includes the step of:
   providing a plastic covering surrounding said first structure and said metallic ankh inset therein, said covering containing a yellow color pigment, and
further comprising the step of:
   enhancing the steps of channelizing energy and transmitting energy with said covering.

* * * * *